United States Patent
Kiani et al.

(10) Patent No.: US 11,103,143 B2
(45) Date of Patent: *Aug. 31, 2021

(54) OPTICAL-BASED PHYSIOLOGICAL MONITORING SYSTEM

(71) Applicant: Masimo Corporation, Irvine, CA (US)

(72) Inventors: Massi Joe E. Kiani, Laguna Niguel, CA (US); Michael O'Reilly, San Jose, CA (US)

(73) Assignee: Masimo Corporation, Irvine, CA (US)

( * ) Notice: Subject to any disclaimer, the term of this patent is extended or adjusted under 35 U.S.C. 154(b) by 133 days.

This patent is subject to a terminal disclaimer.

(21) Appl. No.: 16/521,950

(22) Filed: Jul. 25, 2019

(65) Prior Publication Data

US 2020/0037891 A1 Feb. 6, 2020

Related U.S. Application Data

(63) Continuation of application No. 15/802,172, filed on Nov. 2, 2017, now Pat. No. 10,398,320, which is a
(Continued)

(51) Int. Cl.
*A61B 5/0205* (2006.01)
*A61B 5/00* (2006.01)
*A61B 5/318* (2021.01)
*A61B 5/369* (2021.01)
*A61B 5/1455* (2006.01)
(Continued)

(52) U.S. Cl.
CPC .......... *A61B 5/0205* (2013.01); *A61B 5/1455* (2013.01); *A61B 5/318* (2021.01); *A61B 5/369* (2021.01); *A61B 5/4821* (2013.01); *A61B 5/4839* (2013.01); *A61B 5/7278* (2013.01); *A61B 5/7282* (2013.01); *A61B 5/743* (2013.01);
(Continued)

(58) Field of Classification Search
CPC ....... A61B 5/0205; A61B 5/318; A61B 5/369; A61B 5/4839; A61B 5/7278; A61B 5/743; A61B 5/1455; A61B 5/4821; A61B 5/021; A61B 5/024; A61B 5/0816; A61B 5/087
See application file for complete search history.

(56) References Cited

U.S. PATENT DOCUMENTS 4,421,122 A 12/1983 Duffy
4,960,128 A 10/1990 Gordon et al.
(Continued)

OTHER PUBLICATIONS

Hager et al. The Perfusion Index Measured by a Pulse Oximeter Indicates Pain Stimuli in Anesthetized Volunteers, ASA Abstract 2003, Anesthesiology 2004; 101: A514 (Year: 2003).*

*Primary Examiner* — Jennifer Pitrak McDonald
*Assistant Examiner* — Shreya Anjaria
(74) *Attorney, Agent, or Firm* — Knobbe Martens Olson & Bear LLP

(57) ABSTRACT

A non-invasive, optical-based physiological monitoring system is disclosed. In an embodiment, the non-invasive, optical-based physiological monitoring system comprises an emitter configured to emit light into a tissue site of a living patient; a detector configured to detect the emitted light after attenuation by the tissue site and output a sensor signal responsive to the detected light; and a processor configured to determine, based on the sensor signal, a first physiological parameter indicative of a level of pain of the patient.

12 Claims, 8 Drawing Sheets

Related U.S. Application Data continuation of application No. 15/347,190, filed on Nov. 9, 2016, now Pat. No. 9,833,152, which is a continuation of application No. 14/479,083, filed on Sep. 5, 2014, now Pat. No. 9,517,024, which is a continuation of application No. 12/885,430, filed on Sep. 17, 2010, now abandoned.

(60) Provisional application No. 61/243,161, filed on Sep. 17, 2009.

(51) Int. Cl.
  *A61B 5/021* (2006.01)
  *A61B 5/024* (2006.01)
  *A61B 5/08* (2006.01)
  *A61B 5/087* (2006.01)

(52) U.S. Cl.
  CPC .............. *A61B 5/021* (2013.01); *A61B 5/024* (2013.01); *A61B 5/087* (2013.01); *A61B 5/0816* (2013.01)

(56) References Cited

U.S. PATENT DOCUMENTS

| | | |
|---|---|---|
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,286,252 A | 2/1994 | Tuttle et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| 5,441,528 A | 8/1995 | Chang |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,544,661 A | 8/1996 | Davis |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,694,939 A | 12/1997 | Cowings |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,018,682 A | 1/2000 | Rise |
| 6,027,452 A | 2/2000 | Flaherty et al. |
| 6,036,642 A | 3/2000 | Diab et al. |
| 6,045,509 A | 4/2000 | Caro et al. |
| 6,047,203 A | 4/2000 | Sackner et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,631,291 B2 | 10/2003 | Viertiö-Oja et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |

(56) References Cited

U.S. PATENT DOCUMENTS

| | | |
|---|---|---|
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,768,920 B2 | 7/2004 | Lange et al. |
| 6,770,028 B1 | 8/2004 | Ali et al. |
| 6,771,994 B2 | 8/2004 | Kiani et al. |
| 6,792,300 B1 | 9/2004 | Diab et al. |
| 6,807,965 B1 * | 10/2004 | Hickle ............... A61B 5/417 128/204.23 |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,089,927 B2 | 8/2006 | John et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,146,211 B2 | 12/2006 | Frei et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,277,758 B2 | 10/2007 | DiLorenzo |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,299,088 B1 | 11/2007 | Thakor |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,373,198 B2 | 5/2008 | Bibian et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,715,919 B2 | 5/2010 | Osorio et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,783,343 B2 | 8/2010 | Särkelä et al. |
| 7,791,155 B2 | 9/2010 | Diab |
| 7,801,581 B2 | 9/2010 | Diab |
| 7,811,279 B2 | 10/2010 | John |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |

(56) References Cited

U.S. PATENT DOCUMENTS

| | | |
|---|---|---|
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,187,181 B2 | 5/2012 | Osorio et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |

(56) References Cited

U.S. PATENT DOCUMENTS

| | | |
|---|---|---|
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 * | 12/2016 | Kiani ............... A61B 5/369 |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |

(56) References Cited

U.S. PATENT DOCUMENTS

| | | |
|---|---|---|
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 * | 12/2017 | Kiani .................... A61B 5/369 |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| D833,624 S | 11/2018 | DeJong et al. |
| 10,123,726 B2 | 11/2018 | Al-Ali et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,398,320 B2 * | 9/2019 | Kiani .................... A61B 5/4839 |
| 2002/0099409 A1 | 7/2002 | Hui |
| 2002/0173729 A1 * | 11/2002 | Viertio-Oja ............ A61B 5/374 |
| | | 600/544 |
| 2004/0010203 A1 | 1/2004 | Bibian et al. |
| 2004/0015091 A1 * | 1/2004 | Greenwald .......... A61B 5/4821 |
| | | 600/513 |
| 2004/0092809 A1 | 5/2004 | DeCharms |
| 2004/0116784 A1 | 6/2004 | Gavish |
| 2005/0070823 A1 | 3/2005 | Donofrio et al. |
| 2005/0113744 A1 | 5/2005 | Donoghue |
| 2005/0277819 A1 | 12/2005 | Kiani et al. |
| 2006/0161054 A1 | 7/2006 | Reuss et al. |
| 2007/0010755 A1 | 1/2007 | Sarkela |
| 2007/0021673 A1 | 1/2007 | Arbel |
| 2007/0287931 A1 | 12/2007 | Dilorenzo |
| 2008/0033490 A1 | 2/2008 | Giftakis |
| 2008/0103375 A1 | 5/2008 | Kiani |
| 2008/0188760 A1 * | 8/2008 | Al-Ali .................... G16H 50/20 |
| | | 600/507 |
| 2008/0300471 A1 | 12/2008 | Al-Ali |
| 2008/0317672 A1 | 12/2008 | Viertio-Oja |
| 2009/0069642 A1 * | 3/2009 | Gao ........................ H04L 67/12 |
| | | 600/300 |
| 2009/0099627 A1 | 4/2009 | Molnar |
| 2009/0247984 A1 | 10/2009 | Lamego et al. |
| 2009/0264789 A1 | 10/2009 | Molnar |
| 2009/0275813 A1 | 11/2009 | Davis |

(56) References Cited

U.S. PATENT DOCUMENTS

| | | |
|---|---|---|
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0030089 A1 | 2/2010 | Hyde |
| 2010/0100036 A1 | 4/2010 | Leuthardt |
| 2010/0261979 A1 | 10/2010 | Kiani |
| 2011/0082711 A1 | 4/2011 | Poeze et al. |
| 2011/0087081 A1 | 4/2011 | Kiani et al. |
| 2011/0125060 A1 | 5/2011 | Telfort et al. |
| 2011/0172561 A1 | 7/2011 | Kiani et al. |
| 2011/0208015 A1 | 8/2011 | Welch et al. |
| 2011/0208018 A1 | 8/2011 | Kiani |
| 2011/0230733 A1 | 9/2011 | Al-Ali |
| 2011/0245633 A1 | 10/2011 | Goldberg et al. |
| 2012/0165629 A1 | 6/2012 | Merritt et al. |
| 2012/0209084 A1 | 8/2012 | Olsen et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0296672 A1 | 11/2013 | O'Neil et al. |
| 2013/0324808 A1 | 12/2013 | Al-Ali et al. |
| 2013/0331660 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330098 A1 | 11/2014 | Merritt et al. |
| 2014/0357966 A1 | 12/2014 | Al-Ali et al. |
| 2014/0378784 A1 | 12/2014 | Kiani |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0257689 A1 | 9/2015 | Al-Ali et al. |
| 2015/0351697 A1 | 12/2015 | Weber et al. |
| 2015/0359489 A1 | 12/2015 | Baudenbacher |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0103598 A1 | 4/2016 | Al-Ali et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0270735 A1 | 9/2016 | Diab et al. |
| 2016/0283665 A1 | 9/2016 | Sampath et al. |
| 2016/0287786 A1 | 10/2016 | Kiani |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0014083 A1 | 1/2017 | Diab et al. |
| 2017/0024748 A1 | 1/2017 | Haider |
| 2017/0042488 A1 | 2/2017 | Muhsin |
| 2017/0055847 A1 | 3/2017 | Kiani et al. |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0196464 A1 | 7/2017 | Jansen et al. |
| 2017/0196470 A1 | 7/2017 | Lamego et al. |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0311891 A1 | 11/2017 | Kiani et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |

(56) References Cited

U.S. PATENT DOCUMENTS

| | | |
|---|---|---|
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |

* cited by examiner

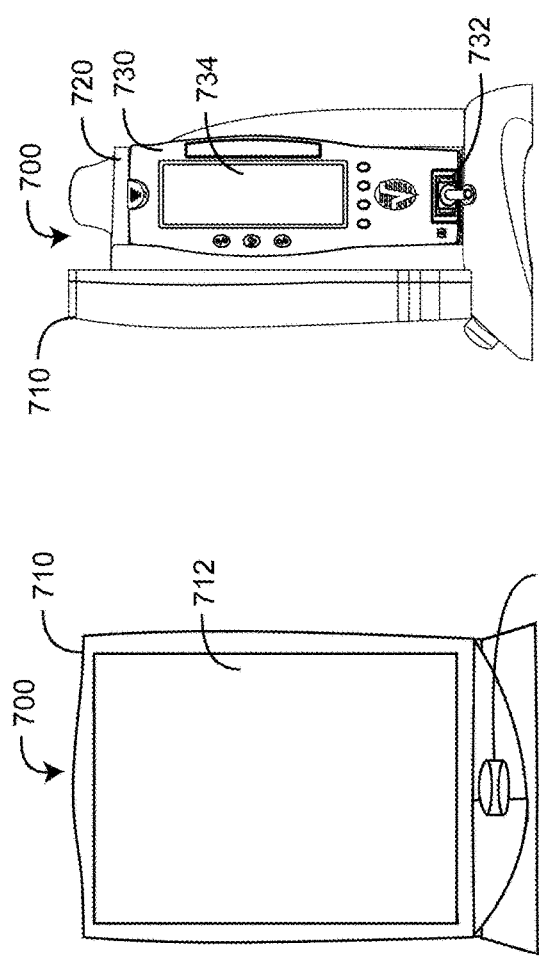
FIG. 7B
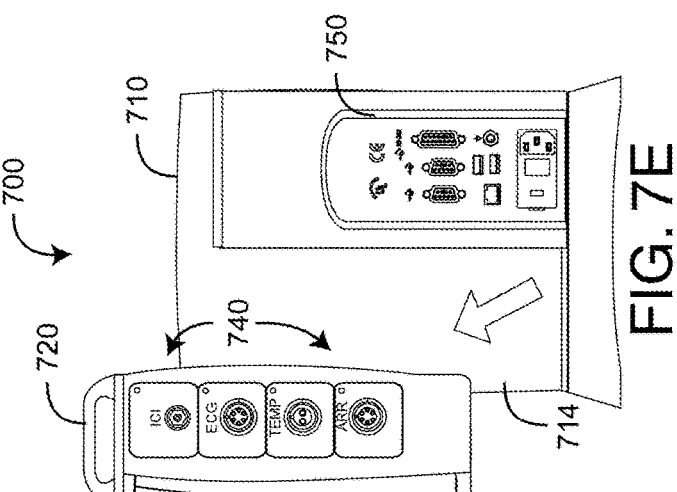
FIG. 7E
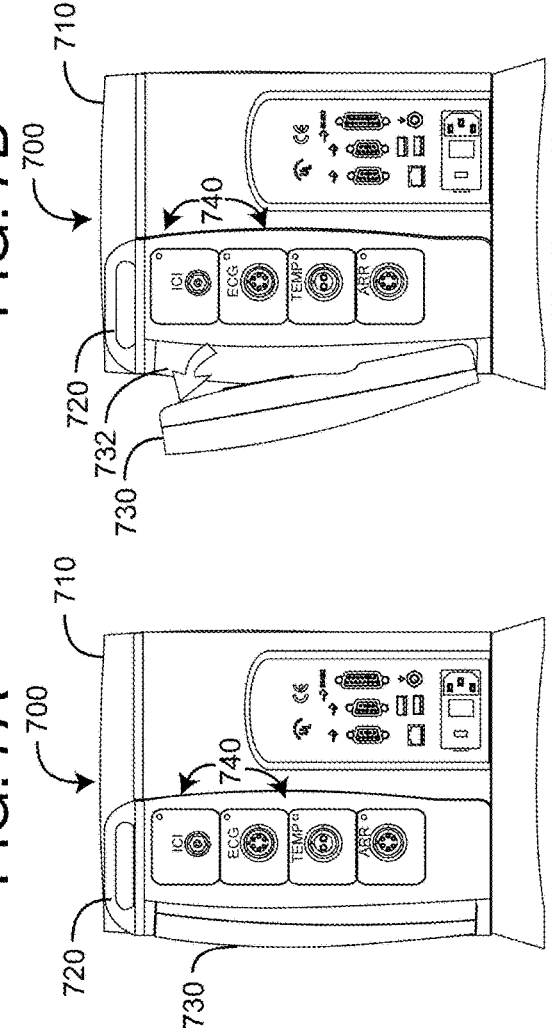
FIG. 7A
FIG. 7D
FIG. 7C

OPTICAL-BASED PHYSIOLOGICAL MONITORING SYSTEM

CROSS-REFERENCE TO RELATED APPLICATIONS

This application is a continuation of U.S. patent application Ser. No. 15/802,172, filed Nov. 2, 2017, and titled "Optical-Based Physiological Monitoring System," which is a continuation of U.S. patent application Ser. No. 15/347,190, filed Nov. 9, 2016, and titled "Optical-Based Physiological Monitoring System," which is a continuation of U.S. patent application Ser. No. 14/479,083, filed Sep. 5, 2014, and titled "Optical-Based Physiological Monitoring System," which is a continuation of U.S. patent application Ser. No. 12/885,430, filed Sep. 17, 2010, and titled "Pharmacological Management System," which claims priority benefit under 35 U.S.C. § 119(e) to U.S. Provisional Patent Application No. 61/243,161, filed Sep. 17, 2009, and titled "Pharmacological Management System." The entire disclosure of each of the above items is hereby made part of this specification as if set forth fully herein and incorporated by reference for all purposes, for all that it contains.

Any and all applications for which a foreign or domestic priority claim is identified in the Application Data Sheet as filed with the present application are hereby incorporated by reference under 37 CFR 1.57.

BACKGROUND

Generation and analysis of an electroencephalogram (EEG) is a widely accepted noninvasive procedure for diagnosing a person's neurological system. For example, an EEG can reflect changes in a brain's cellular function due to insufficient oxygen or drugs, to name a few. An EEG system consists of a bio-potential sensor and corresponding monitor to process, analyze and display an EEG signal and corresponding neurological parameters. A bio-potential sensor responds to the electrical potential difference between at least two well-spaced electrodes, using a separate ground electrode. The biopotential monitor typically displays the EEG waveform and a numerical index that reflects changes in the EEG bandwidth and power.

Generation and analysis of a photoplethysmograph is a widely accepted noninvasive procedure for diagnosing a person's cardiovascular system. For example, a photoplethysmograph can yield the oxygen saturation level of arterial blood, an indicator of a person's oxygen supply. A pulse oximetry system consists of an optical sensor applied to a fleshy tissue site, such as a fingertip, and a corresponding pulse oximetry monitor (pulse oximeter). Using multiple wavelength light emitting diodes and a corresponding detector, the optical sensor measures the light absorption of the pulsatile blood at the tissue site. In particular, the optical sensor is responsive to the instantaneous blood volume as well as the blood constituency. Accordingly, the pulse oximeter typically displays a numerical readout of a person's oxygen saturation and pulse rate along with an audible indication of the person's pulse. The photoplethysmograph waveform may also be displayed.

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad8®, Rad5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Masimo Laboratories, Irvine, Calif. (Masimo Labs) and all incorporated by reference herein. Advanced blood parameter measurement systems include Masimo Rainbow® SET, which provides measurements in addition to $SpO_2$, such as total hemoglobin (SpHb™), oxygen content (SpOC™) methemoglobin (SpMet), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad87™ and Rad57™ monitors, all available from Masimo. Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

SUMMARY

Depth of consciousness (DOC) is an important physiological assessment during the administration of anesthesia and analgesia drugs. For example, an overdose of anesthesia risks physical impairment or death. An underdose of anesthesia risks "surgical awareness." A DOC index is typically derived by an EEG sensor measurement of electrical activity in the cerebral cortex. Advantageously, the measurement of various cardio-vascular system and respiratory system responses can substitute for or supplement typical central nervous system measures of consciousness, providing improved resolution and accuracy. For example, cardiovascular system and respiratory system parameters responsive to consciousness may include perfusion index (PI), plethysmograph variability index (PVI), heart rate (HR), blood pressure (BP) and respiration rate (RR), to name a few.

Level of pain (LOP) is also an important physiological assessment during anesthesia and analgesia. A LOP index is an advantageous quantization of pain that allows proper dosing of administered drugs. Advantageously, a LOP index may also be derived from various cardiovascular system and respiratory system parameters, such as those cited above.

Although dissimilar physiological phenomena, there is an important relationship between consciousness and pain for anesthesia and analgesia applications. During anesthesia, it is desirable to ensure that pain is eliminated during apparent unconsciousness. During analgesia, it is desirable for pain to be diminished or eliminated without impinging on consciousness. Accordingly, parameters useful in conjunction with consciousness assessment may be useful in conjunction with pain assessment and vice-a-versa.

A pharmacological management system advantageously provides sensors and processors to measure and analyze both DOC and LOP. Accordingly, a pharmacological management system advantageously senses and analyzes both consciousness and pain related physiological signals so as to generate multidimensional parameters or indexes indicative of both physiological processes.

One aspect of a pharmacological management system comprises sensors, a pharmacological status monitor and a drug administrator. The sensors attach to the patient so as to generate corresponding sensor signals. The pharmacological status monitor is responsive to the sensor signals so as to generate an output indicative of the drug-induced effects of the pharmacological agent on the patient. Further, the monitor output is fed-back to the drug administrator so as to regulate administration of the agent for a desired effect.

In various embodiments, the monitor comprises a hematological processor responsive to an optical sensor signal and a neurological processor responsive to a bio-potential sensor. The hematological processor has a photoplethysmograph input and provides a level of pain output to the pharmacological status monitor. The neurological processor has an EEG input and provides a depth of consciousness output to the pharmacological status monitor. The pharmacological status monitor generates a control output to a drug-infusion pump. The level of pain output is a perfusion index. The pharmacological status monitor generates a combined index related to both depth of consciousness and level of pain.

Another aspect of a pharmacological management system is inputting sensor signals derived from a patient and calculating physiological parameters accordingly. The sensor signals provide measurements of physiological systems. Physiological parameters are calculated from the sensor signals. The parameters are operated on to generate monitor outputs, which are indicative of levels of both consciousness and pain.

In various embodiments, a first sensor signal is utilized to generate a consciousness index and a second sensor signal is utilized to generate a perfusion index. Cues are displayed to indicate a patient with a stable or unstable physiological condition. Outputs control drug-infusion equipment or medical gas ventilation equipment. Patient wellness is diagnosed.

A further aspect of a pharmacological management system measures physiological parameters derived from at least some of a patient's central nervous system, respiratory system and cardio-vascular system so as to assess level of pain and depth of consciousness during the administration of anesthetic and analgesic agents. The pharmacological management system comprises sensors in communications with a patient so as to generate sensor signals and a monitor front-end in communications with the sensor signals so as to generate digitized sensor signals. A signal processor is in communications with the front-end so as to generate physiological parameters. The signal processor derives an electrical-based depth of consciousness (DOC) indicator from an electrical one of the sensors in communications with the patient's central nervous system and a pleth-based level of pain (LOP) indicator from an optical one of the sensors in communications with the patient's cardio-vascular system. An instrument manager generates a monitor output in response to a combination of the DOC indicator and the LOP indicator.

In various embodiments, a drug administrator administers a pharmacological agent to the patient and is responsive to the monitor output. The LOP indicator is responsive to a perfusion index (PI) parameter or a plethysmograph variability index (PVI) parameter. The monitor output comprises an electronic signal to the drug administrator that affects the dose of pharmacological agent. The monitor output also comprises a combined display of LOP and DOC.

BRIEF DESCRIPTION OF THE DRAWINGS

FIGS. 7A-E are illustrations of a pharmacological status monitor embodiment responsive to various sensors.

DETAILED DESCRIPTION

Figure 1:
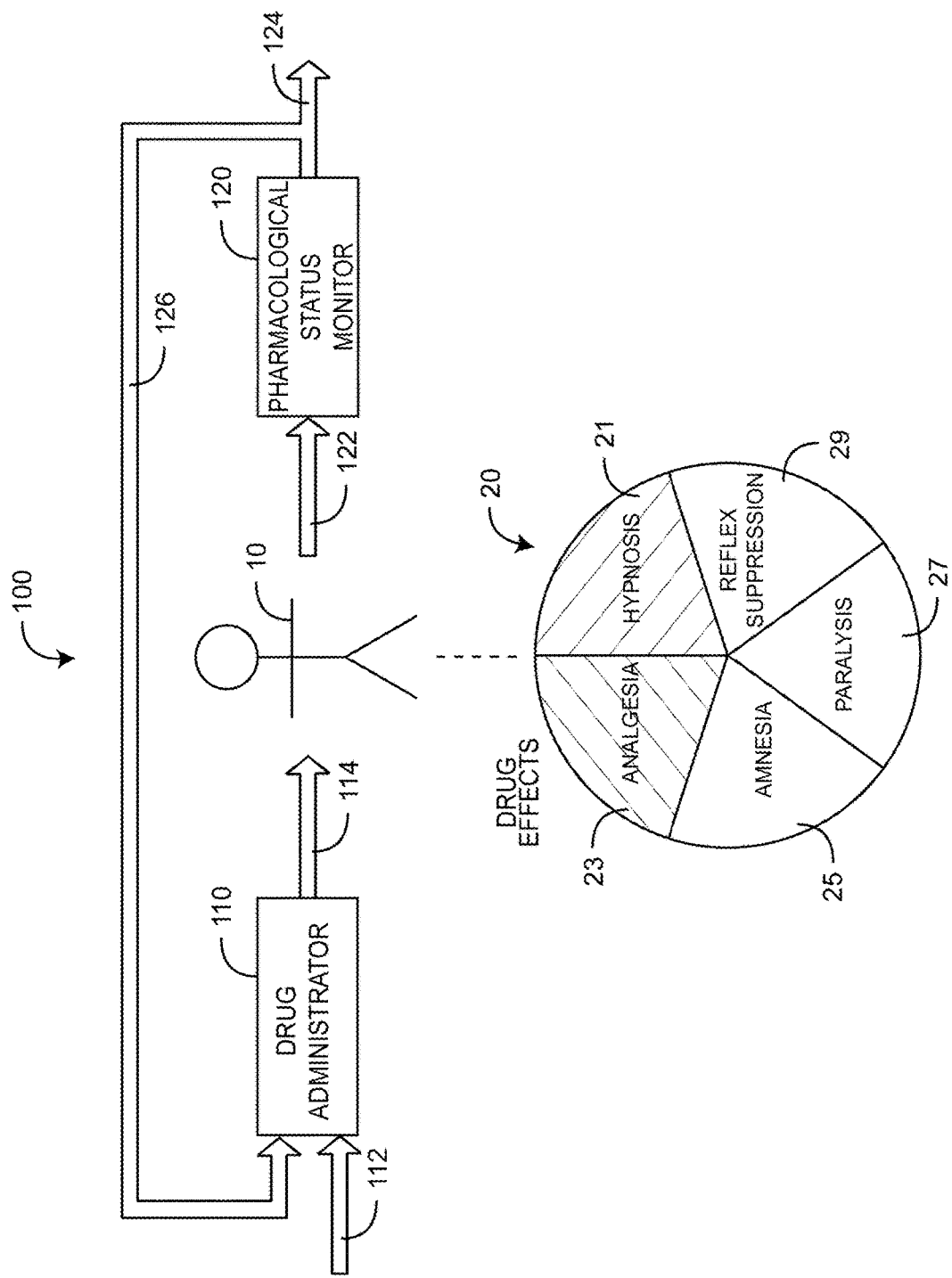
FIG. 1 is a general block diagram of pharmacological management system.

FIG. 1 generally illustrates a pharmacological management system 100 having a drug administrator 110 that provides a pharmacological agent 114 to a patient 10 and a pharmacological status monitor 120 responsive to corresponding drug-induced effects 20. Pharmacological agents 114 may be, as examples, anesthesia or analgesia drugs. For anesthesia applications, the desired effect 20 may be general anesthesia or various levels of sedation. The drug administrator 110 may vary from a healthcare provider manually administering drugs to an automatic or semi-automatic machine such as a drug infusion device or medical gas inhalation device. The drug administrator may be responsive to external controls 112, such as manual inputs or electronic signals.

As shown in FIG. 1, drug-induced effects 20 in the patient 10 may include hypnosis 21, analgesia 23, amnesia 25, paralysis 27 and reflex suppression 29. Hypnosis 21 produces unconsciousness; analgesia 23 blocks the conscious sensation of pain; amnesia 25 prevents memory formation; paralysis 27 prevents unwanted movement or muscle tone; and reflex suppression 29 prevents exaggerated autonomic reflexes. For general anesthesia, some or all of these drug-induced effects 20 may be the goal. For low-level sedation, the goal may be to achieve some effects 20 while suppressing others. For pain reduction, analgesia 23 is the goal along with minimization of other drug-induced effects 20.

Also shown in FIG. 1, the pharmacological management system 100 advantageously assists healthcare providers to achieve the above-stated goals, among others. Sensors (not shown) attached to the patient 10 provide biological signals 122 to the pharmacological status monitor 120. The monitor 120 processes these signals 122 and generates outputs 124 indicative of the effects 20 of administered pharmacological agents 114. The outputs 124 may be displays, alarms, controls or indicators, for example. The outputs 124 may also provide manual or automatic feedback 126 to the drug administrator 110 so as to regulate administration of the agent 114 for the desired effects 20.

Figure 2:
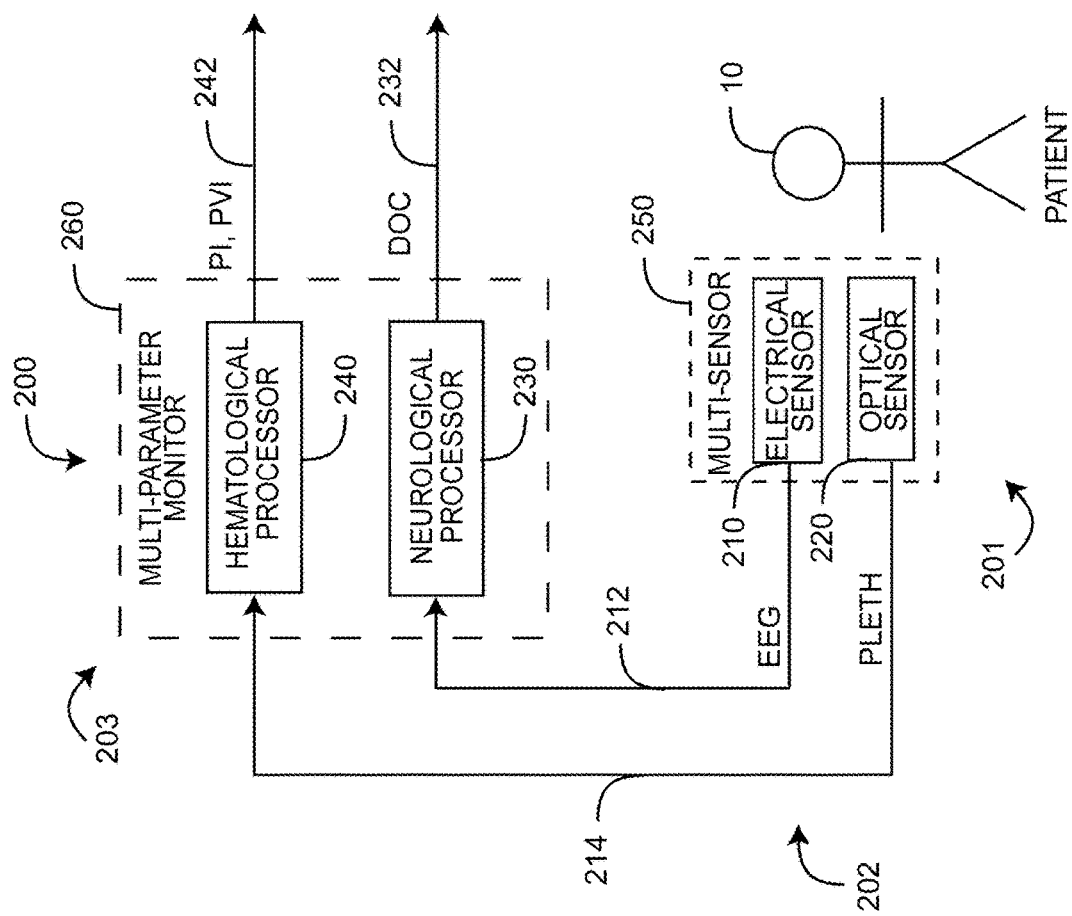
FIG. 2 is a block diagram of a pharmacological management system embodiment responsive to electrical and optical sensors so as to measure consciousness and pain.

FIG. 2 illustrates a pharmacological management system 200 having sensors 201 in communications with a patient 10. The sensors 201 generate sensor waveforms 202 to corresponding monitors 203. The monitors 203 process the waveforms 202 so as to calculate parameters that alone or in combination are indicative of the pharmacological status of the patient 10. In one embodiment, sensors 201 include an electrical (biopotential) sensor 210 placed proximate the head so as to generate an EEG waveform 212 and an optical sensor 220 placed on a fleshy tissue site so as to generate a photoplethysmograph 214.

A neurological monitor 230 processes the EEG waveform 212 to generate a first parameter 232 related to depth of consciousness (DOC). In an embodiment, the first parameter 232 is a dimensionless index that reflects the level of activity of the cerebral cortex. In a particular embodiment, the first parameter 232 is a Bispectral Index™ (BIS) proprietary to Aspect Medical Systems, Inc., Norwood, Mass. ("Aspect"), and the neurological processor 230 is a BIS module also proprietary to Aspect. In another particular embodiment, the first parameter 232 is a Patient State Index™ (PSI) proprietary to Hospira, Inc., Lake Forest, Ill. ("Hospira"), and the neurological processor 230 is a SEDLine monitor or module, also proprietary to Hospira.

A hematological monitor 240 processes the photoplethysmograph (pleth) waveform 214 to generate at least one second parameter 242. In an embodiment, the second parameter is a level of pain (LOP) index. In an embodiment, the second parameter is a pleth-based DOC index providing improved resolution and accuracy in determining DOC compared to only an EEG-based DOC index. In an embodiment, the second parameter 242 is a Perfusion Index (PI) or a Plethysmograph Variability Index (PVI) proprietary to Masimo Corporation, Irvine, Calif. ("Masimo") or both, and the hematological processor 240 is any of various monitors or modules available from Masimo, such as described above. PI may change dramatically in response to sympathetic changes in vasoconstriction or vasodilation of peripheral vessels reflective of consciousness or pain. PI comprises a relative indication of pulse strength at a monitoring site. For example, PI may be defined as the ratio of a pleth AC value to its DC value, or the percentage of pulsatile signal to non-pulsatile signal. PVI is described in U.S. patent application Ser. No. 11/952,940 filed Dec. 7, 2007 titled Plethysmograph Variability Index, assigned to Masimo and incorporated by reference herein.

As shown in FIG. 2, in an embodiment the electrical sensor 210 is any of various EEG sensors having multiple biopotential electrodes for placement across various head sites for detection of electrical signals originating in the brain. In an embodiment, the optical sensor 220 is any of various blood parameter sensors having LED emitters and at least one photodiode detector for placement at various fleshy tissue sites for detection of pulsatile blood flow and in particular the measurement of optical properties thereof, such as absorption, reflection, transmission and transflectance to name a few. In an embodiment, the optical sensor 220 is any of various optical sensors available from Masimo, such as described above.

Further shown in FIG. 2, in an embodiment, and optical sensor may comprise a combination or multi-sensor 250 that provides both EEG and photoplethysmograph waveforms, such as described with respect to FIGS. 5 and 8, below. In an embodiment, the hematological and neurological monitors may comprise a combination or multi-parameter monitor 260 having hematological and neurological processing plug-ins, modules or similar technology, such as described with respect to FIGS. 6 and 7, below.

Figure 3:
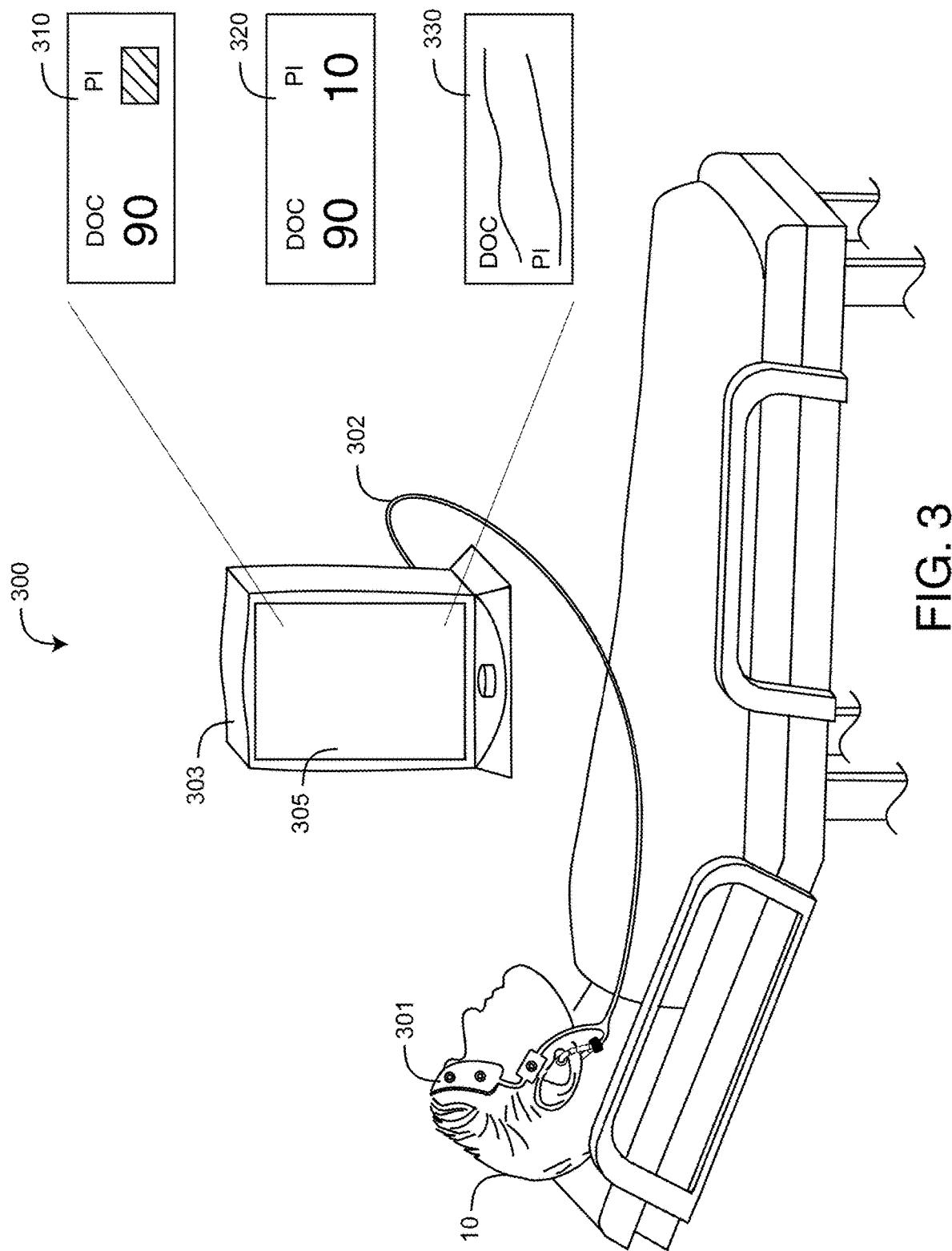
FIG. 3 illustrates a pharmacological management system configured for anesthesia applications.

FIG. 3 illustrates a pharmacological management system 300 configured for anesthesia applications having a sensor 301 attached to a patient 10, a pharmacological status monitor 303 and a sensor cable 302 providing sensor signal communications between the sensor 301 and the monitor 303. In an embodiment, the sensor 301 provides multiple physiological signals to the monitor 303, which derives at least two different measures of consciousness or at least a measurement of consciousness and a measurement of pain. In an embodiment, these physiological signals are EEG and photoplethysmograph signals. In an embodiment, the monitor 303 calculates both a DOC index and PI from the EEG and plethysmograph signals and displays these parameters on the monitor display 305 accordingly.

As shown in FIG. 3, in a mixed display embodiment 310 a DOC parameter is displayed numerically adjacent a LOP parameter displayed as a color. For example, the DOC parameter may be an index, such as BIS, displayed as a dimensionless number. The LOP parameter may be, for example, PI, displayed as a green, yellow or red indicator depending on a preset range of high, medium and low PI values. The low PI value range being set so as to indicate the occurrence of significant vasoconstriction in response to pain or measurable vasodilation in response to increasing depth of consciousness. In a numerical display embodiment 320, DOC and LOP are displayed as proximately located numerical readouts, such as a DOC index and a perfusion index (PI). In a graphical display embodiment 330, DOC and LOP are separately indicated as trends, such as a DOC index trend and a PI trend. The monitor may also calculate a combined index related to consciousness or pain or both. Other individual or combined parameter displays include any of various readouts, graphs, charts or indicators in any of various single or multiple colors. The above monitoring and display embodiments advantageously assist an anesthesiologist or other administrator of drugs to titrate anesthesia based upon either multiple indicators of DOC or on indicators of DOC and LOP. This dual monitoring of pain and consciousness during administration of anesthesia drugs advantageously increases monitor responsivity to under or over dosing of anesthesia.

Figure 4:
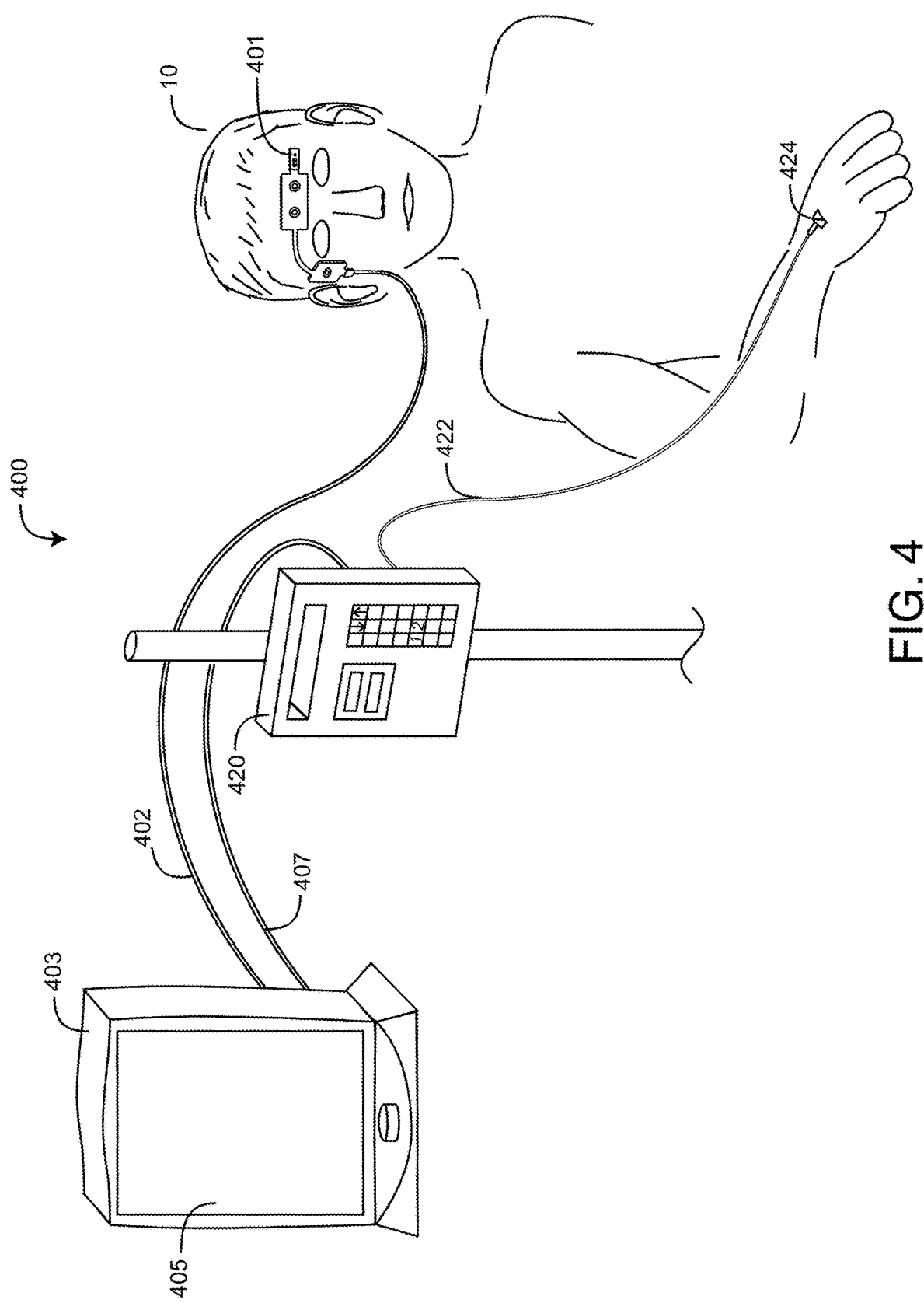
FIG. 4 illustrates a pharmacological management system configured for analgesia applications.

FIG. 4 illustrates a pharmacological management system 400 configured for analgesia applications, such as patient controlled analgesia (PCA). In particular, the pharmacological management system 400 has a sensor 401 attached to a patient 10, a pharmacological status monitor 403 and a sensor cable 402 providing sensor signal communications between the sensor 401 and the monitor 403. Further, the monitor 403 generates control signals via a control cable 407 to the drug-infusion pump 420. The drug-infusion pump 420 administers drugs to the patient 10 via a tube 422 and an IV 424. A patient-actuated controller (not shown) generates drug administration requests to the drug-infusion pump 420 via cable or wireless communications. In this manner, the pump 420 responds to patient perceived pain levels. In particular, the patient 10 actuates the controller, such as via a button press, so as to signal the drug-infusion pump 420 to administer a measured analgesia dose. The pump 420 enables or pauses patient-controlled dosing according to monitor 403 signals transmitted via the control cable 407. These control signals are responsive to monitor calculated DOC and LOP related parameters. Further, these parameters are displayed on a monitor screen 405, such as described with respect to FIG. 3, above.

The sensor 401 provides physiological signals to the monitor 403 related to depth of consciousness (DOC) or level of pain (LOP). In an embodiment, these physiological signals are EEG and photoplethysmograph signals. The monitor 403 calculates DOC, LOP or a combination consciousness and pain parameters from the EEG and plethysmograph signals and processes those parameters to generate control outputs 407 to the drug-infusion pump 420. In this manner, the administration of analgesia is controlled not only according to the patient's perceived pain level, but also according to a physiologically indicated pain level and to avoid consciousness impairment. In a particular embodiment, LOP is indicated by a perfusion index (PI), as described above, and PCA is paused or enabled according to a rising or falling PI, respectively, or according to a DOC index, or both.

Figure 5B:
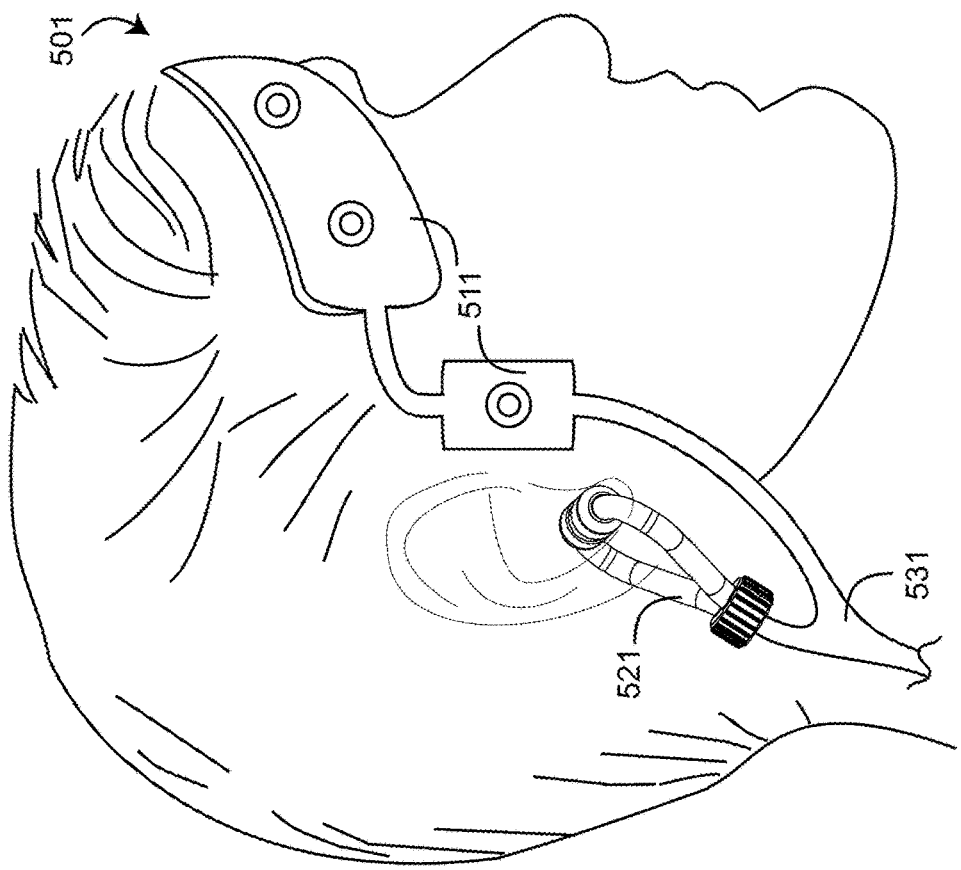
FIGS. 5A-B are illustrations of combination sensor embodiments for measuring both consciousness and pain.
Figure 5A:
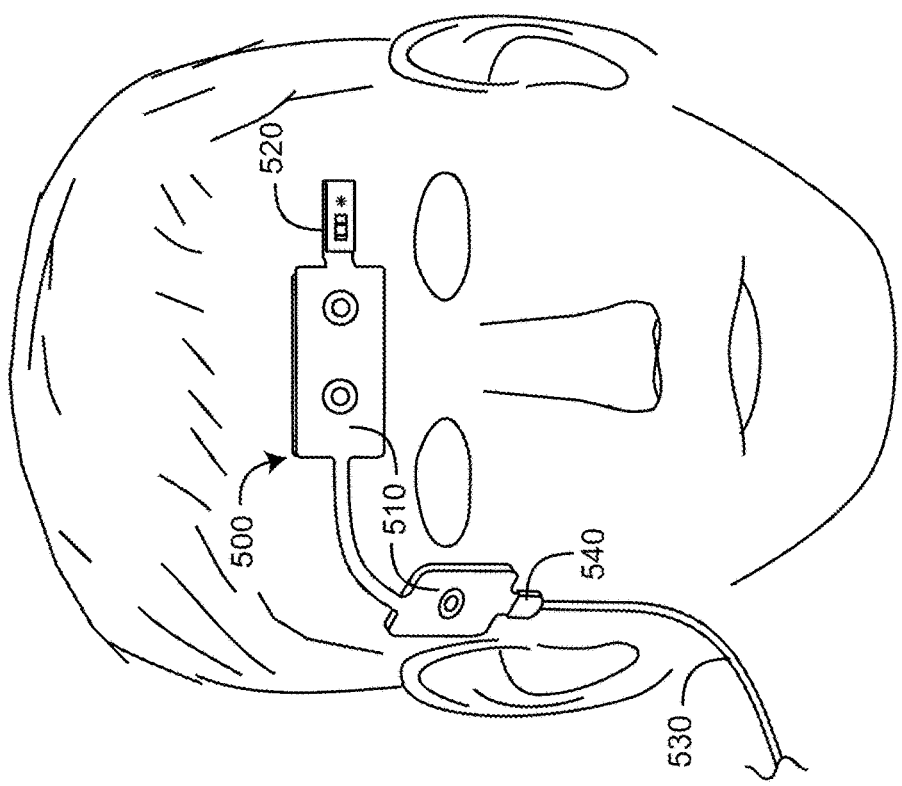

FIGS. 5A-B illustrate combination sensors, which provide inputs to a pharmacological status monitor having both hematological and neurological signal processors, such as described with respect to FIG. 2, above. FIG. 5A illustrates a combination sensor 500 applied to the forehead and temple areas of a person. The sensor 500 includes an electrical or more specifically a biopotential sensor 510 and an optical sensor 520. A patient cable 530 connects the sensor to one or more monitoring devices (not shown), such as described with respect to FIGS. 7A-E, below. The biopotential sensor 510 may be an EEG sensor for depth of consciousness monitoring, as described above. The optical sensor 520 may be a pulse oximetry reflectance sensor for consciousness or pain monitoring via perfusion index (PI) or other blood parameter, also as described above. The patient cable 530 may connect near the person's temple, as shown, or as an alternative near the person's forehead. The biopotential sensor 510 and optical sensor 520 may share a common connector 540 or each sensor may have a dedicated patient cable connector. Combination EEG and pulse oximetry sensors are described in U.S. Pat. No. 6,934,570, issued Aug. 23, 2005, titled Physiological Sensor Combination and incorporated by reference herein.

FIG. 5B illustrates a combination sensor 501 applied to the forehead, temple and ear concha areas of a person. In one embodiment, the sensor 501 includes a biopotential sensor 511, an optical sensor 521 and a cable 531 that connects the sensor 501 to one or more monitoring devices (not shown). The biopotential sensor 511 may be an EEG sensor for depth of consciousness monitoring, as described above. The optical sensor 521 may be a pulse oximetry transmissive sensor for level of pain monitoring via perfusion index (PI) or other blood parameter, also as described above. In a particular embodiment, the optical sensor 521 is a "Y"-clip ear sensor that flexes so as to slide over the ear periphery and onto either side of the concha. An emitter and detector located at opposite clip ends can then transmit multiple wavelength light into the concha tissue and detect that light after attenuation by pulsatile blood flow within the concha tissue. Optical ear sensors are described in U.S. Provisional Patent App. No. 61/152,964, filed Feb. 16, 2009, titled Ear Sensor and incorporated by reference herein.

Figure 6:
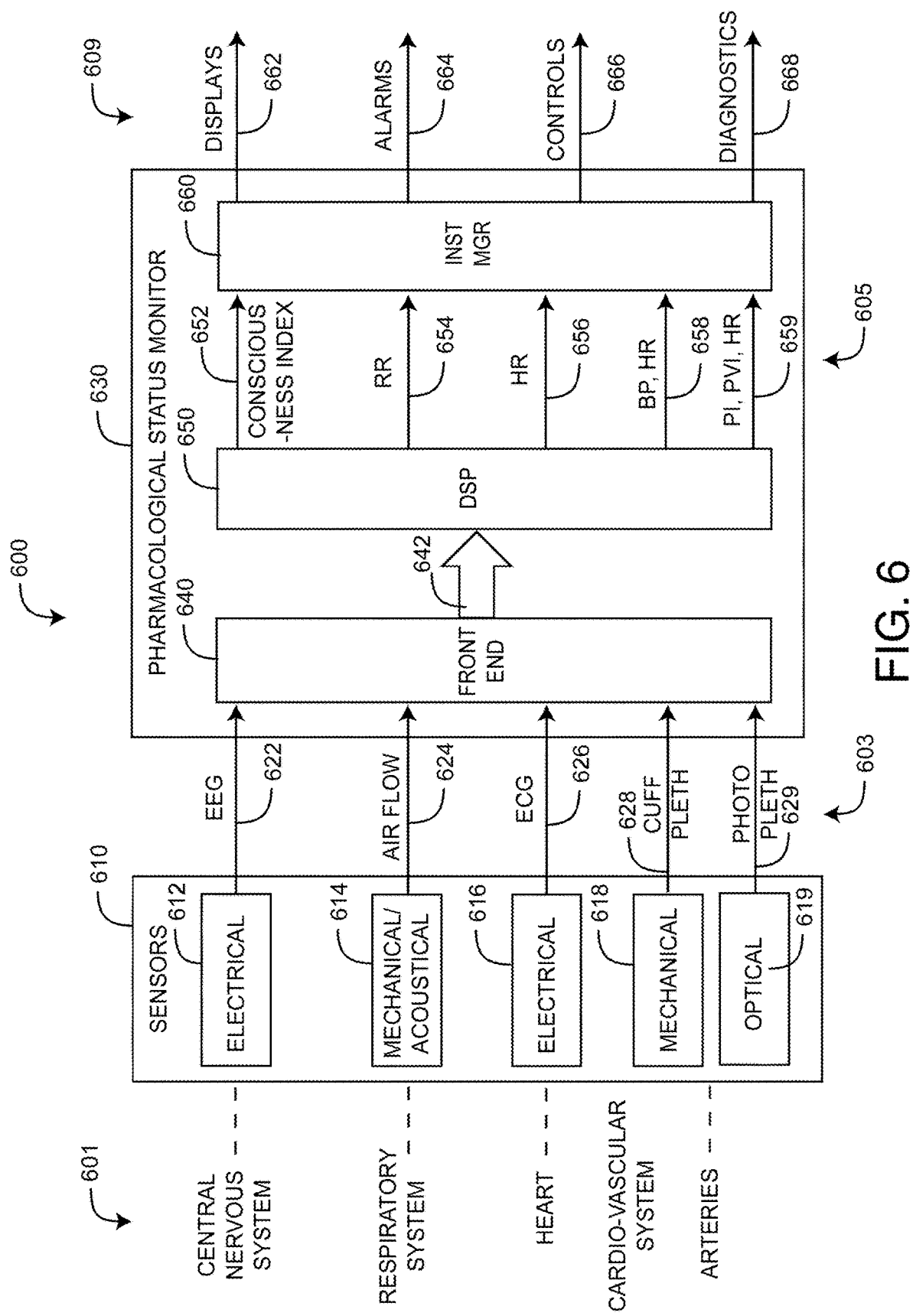
FIG. 6 is a detailed block diagram of a pharmacological management system embodiment.

FIG. 6 illustrates a pharmacological management system 600 embodiment having multiple sensors 610 in communication with a pharmacological status monitor 630. The sensors 610 are responsive to various physiological systems 601 so as to generate various sensor signals 603. A pharmacological status monitor 630 derives physiological parameters 605 from the sensor signals 603 and operates on the parameters 605 to generate monitor outputs 609. The measured physiological systems 601 include one or more of the central nervous system, including the brain; the respiratory system, including the lungs; and the cardio-vascular system, including the heart and arteries. The sensors 610 may include electrical sensors 612, 616, such as bio-potential sensors that generate EEG 622 and ECG 626 signals in response to brain or heart activity, respectively. The sensors 610 may also include mechanical, acoustical, temperature or humidity sensors 614, to name a few, that directly or indirectly measure the inspired or expired air flow 624 from the lungs. Sensors 610 include mechanical sensors 618 that measure arterial blood pressure 628. Sensors 610 further include optical sensors 619 that measure arterial blood flow or volume 629, according to instantaneous light absorption.

Also shown in FIG. 6, parameters 605 are any derived measurements indicative of consciousness or pain or both. Parameters 605 may include a consciousness index 652 derived from an EEG signal 622, such as described with respect to FIG. 2, above. Parameters 605 may also include a perfusion index (PI) 659 indicative of pain and derived from a photoplethysmograph signal 629, also described with respect to FIG. 2, above. Other pain indicative parameters may include respiration rate (RR) 654 derived from a respiratory air flow signal 624; heart rate (HR) 656, 658, 659 derived from an ECG 626, cuff plethysmograph 628 or photoplethysmograph 629; and blood pressure (BP) 658 derived from a pressure plethysmograph 628.

In addition, FIG. 6 shows outputs 609 including displays 662, alarms 664, controls 666 and diagnostics 668. Alarms 664 may be, for example, audible or visual alerts warning of critical conditions that need immediate attention. Controls 666 may be any of various electrical or electronic, wired or wireless or mechanical outputs, to name a few, capable of interfacing with and affecting another device. As examples, controls 666 may interface with drug-infusion equipment or medical gas ventilation equipment, as described above. Diagnostics, including wellness indices, may be audible or visual cues indicating a patient with a stable or unstable physiological condition. Visual cues may be any of various digital readouts, bar graphs, trend graphs, color indicators and the like. Audible cues may be any of various sounds or tones, whether intermittent or continuous or constant or varying in volume.

As shown in FIG. 6, the monitor 630 has a sensor front end 640, one or more digital signal processors (DSP) 650 and one or more instrument managers 660. In an embodiment, the sensor front end 640 may have one or more of various preamps, signal conditioning and analog-to-digital conversion (ADC) that amplify, filter and digitize the sensor signals 603 so as to output digital data channels 642 to a DSP 650. In an embodiment, the DSP 650 comprises a processing device, such as one based on the Super Harvard ARChitecture ("SHARC") commercially available from Analog Devices or any other of a wide variety of data and/or signal processors capable of executing programs for determining physiological parameters from input data. In particular, the DSP 650 includes program instructions capable of receiving multiple channels of data 642 from the sensor front end 640, each channel of which relates to one or more sensor signals 603.

Also shown in FIG. 6, the instrument manager 660 may comprise one or more microcontrollers controlling system management, including, for example, translation and communications of calculated parameter data 605 to various outputs 609. The instrument manager 660 may also act as a watchdog circuit by, for example, monitoring and controlling the activity of the DSP 650.

FIG. 7A-E illustrate a pharmacological status monitor 700 embodiment capable of inputting signals from a wide range of sensors and of deriving a wide range of physiological parameters therefrom including DOC and LOP parameters, such as BIS and PI described with respect to FIG. 2, above, and others described with respect to FIG. 6, above. The pharmacological status monitor 700 has a docking station 710 including a display 712, a removable shuttle 720, a removable handheld 730 and a combination of plug-in modules 740. The docking station 710 has a shuttle port 714 that allows the shuttle station 720 to dock. The shuttle station 720 has a handheld port 732 that allows the handheld monitor 730 to dock. Accordingly, the modular patient monitor 700 has three-in-one functionality including a handheld 730, a handheld 730 docked into a shuttle station 720 as a handheld/shuttle combination and a handheld/shuttle docked into a docking station 710. When docked, the three modules of handheld 730, shuttle 720 and docking station 710 function as one unit. The handheld 730 docked into the shuttle module 720 functions independently of the docking station 710 and expands the handheld parameter capability to the ability to measure all parameters available to the shuttle 720. The docking station 710, in turn, provides the shuttle 720 or handheld/shuttle combination with a large color display 712 and trim knob control 714 in addition to a power supply/communications module 750 having ports for wireless and hardwired communications, Internet access and printers. In an embodiment, the handheld monitor 730 incorporates blood parameter measurement technologies including $SpO_2$, PI, HbCO, HbMet, and Hbt, and the shuttle station 720 incorporates non-blood parameters, such as intelligent cuff inflation (101) for blood pressure measurements, acoustic respiration rate (ARR), ECG and EEG to name a few. A multi-parameter monitor is described in U.S. patent Ser. No. 11/903,746, filed Sep. 24, 2007, titled Modular Patient Monitor and incorporated by reference herein.

Figure 8:
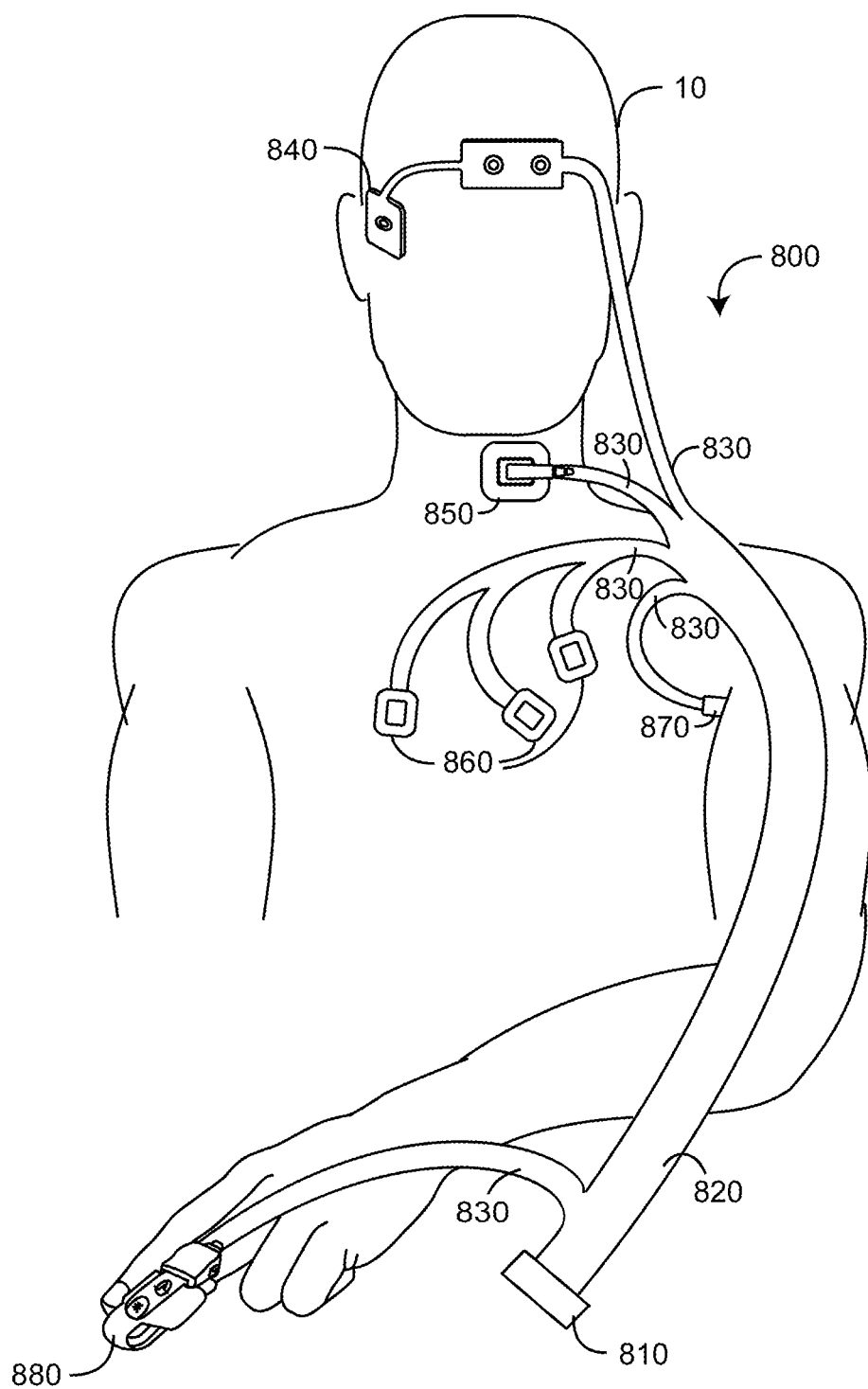
FIG. 8 is an illustration of a multi-sensor embodiment for measuring level of pain and depth of consciousness.

FIG. 8 illustrates an integrated multi-sensor 800 advantageously configured to provide multiple physiological parameter measurements to a pharmacological status monitor 700 (FIGS. 7A-E) via a single connector and interconnected patient cable (not shown). This eliminates the difficulties of a large number of cables and cumbersome connectors when multiple sensors are placed on various areas of a person. In particular, the multi-sensor 800 has a connector 810 in communications with a trunk 820, which fans out to multiple branches 830, each of which terminates in a sensor 840, 850, 860, 870, 880. In an embodiment, the multi-sensor allows measurement of perfusion index (PI) via a pulse oximetry sensor 880 placed on a finger; skin temperature via a thermistor 870 located under an arm; heart rate (HR) via an ECG sensor 860 placed on the chest area; respiration rate (RR) via an acoustic sensor 850 located on the neck to detect airway sounds; and a consciousness index via an EEG sensor 840 placed on the head area.

In other embodiments, other multiple parameter sensors provide sensor inputs to a pharmacological status monitor. A sensor providing both optical and acoustic inputs for blood parameters and acoustic parameters, such as discussed above, in addition to cerebral oximetry, oxygen supply and metabolism among other parameters is described in U.S. Provisional Patent App. No. 61/350,673 titled Opticoustic Sensor filed Jun. 2, 2010, assigned to Masimo and incorporated by reference herein. In particular, the cerebral parameters measured by the opticoustic sensor disclosed therein may provide further indications of LOP and DOC.

A pharmacological management system has been disclosed in detail in connection with various embodiments. These embodiments are disclosed by way of examples only and are not to limit the scope of the claims that follow. One of ordinary skill in the art will appreciate many variations and modifications.

What is claimed is:

1. A physiological monitoring system comprising:
one or more processors configured to:
receive, from a non-invasive optical sensor, a first sensor signal responsive to physiological characteristics of a patient;
receive, from a bio-potential sensor, a second sensor signal responsive to physiological characteristics of the patient;
receive, from an additional sensor, at least a third sensor signal;
determine, based on the first sensor signal, a first physiological parameter indicative of a level of pain of the patient;
determine, based on the second sensor signal, a second physiological parameter indicative of a depth of consciousness of the patient;
determine, based on at least one of the first sensor signal, the second sensor signal, or the third sensor signal, one or more additional physiological parameters indicative of at least one of the level of pain of the patient or the depth of consciousness of the patient, wherein the one or more additional physiological parameters include at least one of: an ECG, a respiration rate, a respiratory air flow, a heart rate, or a blood pressure; and
determine, based on the first physiological parameter, the second physiological parameter, and the one or more additional physiological parameters, a combined index indicative of both the level of pain and the depth of consciousness of the patient.

2. The physiological monitoring system of claim 1, wherein the first physiological parameter comprises a perfusion index.

3. The physiological monitoring system of claim 2, wherein the second physiological parameter comprises an EEG.

4. The physiological monitoring system of claim 3, wherein the combined index is further determined based on an ECG of the patient.

5. The physiological monitoring system of claim 4, wherein the ECG is further indicative of the level of pain of the patient.

6. The physiological monitoring system of claim 5, wherein the one or more processors are further configured to:
determine, based on the first physiological parameter and the ECG of the patient, a combined indication of the level of pain of the patient.

7. The physiological monitoring system of claim 1, wherein the non-invasive optical sensor, the bio-potential sensor, and the additional sensor are in communication with a monitor via a single cable.

8. The physiological monitoring system of claim 7 further comprising:
   the non-invasive optical sensor comprising:
      an emitter configured to emit light into tissue of the patient; and
      a detector configured to detect the emitted light after attenuation by the tissue and output the first sensor signal responsive to the detected light;
   the bio-potential sensor configured to be attached to the patient and configured to output at least the second sensor signal; and
   the additional sensor configured to be attached to the patient and configured to output at least the third sensor signal.

9. The physiological monitoring system of claim 1, wherein the one or more processors are further configured to:
   output feedback to a drug administrator configured to provide a pharmacological agent to the patient, wherein the feedback is outputted to the drug administrator so as to regulate administration of the pharmacological agent for a desired effect, wherein the feedback includes the combined index indicative of both the level of pain and the depth of consciousness of the patient.

10. The physiological monitoring system of claim 1, wherein the one or more processors are further configured to:
   provide a control output to at least one of drug-infusion equipment or medical gas ventilation equipment based at least in part on the combined index indicative of both the level of pain and the depth of consciousness of the patient.

11. The physiological monitoring system of claim 1, wherein the one or more processors are further configured to:
   generate a displayable output including a visual indication of the combined index indicative of both the level of pain and the depth of consciousness of the patient.

12. The physiological monitoring system of claim 11, wherein the visual indication comprises at least one of a number, a color, or a graph.

\* \* \* \* \*